(12) United States Patent
Gupta

(10) Patent No.: US 8,992,528 B2
(45) Date of Patent: Mar. 31, 2015

(54) INTRAMEDULLARY SYSTEM FOR MANAGING A BONE FRACTURE

(76) Inventor: Amit Gupta, Prospect, KY (US)

( * ) Notice: Subject to any disclaimer, the term of this patent is extended or adjusted under 35 U.S.C. 154(b) by 0 days.

(21) Appl. No.: 13/523,449

(22) Filed: Jun. 14, 2012

(65) Prior Publication Data

US 2013/0197518 A1    Aug. 1, 2013

Related U.S. Application Data

(60) Provisional application No. 61/496,658, filed on Jun. 14, 2011.

(51) Int. Cl.

| | | |
|---|---|---|
| *A61B 17/56* | (2006.01) | |
| *A61B 17/58* | (2006.01) | |
| *A61F 2/30* | (2006.01) | |
| *A61B 17/72* | (2006.01) | |
| *A61B 17/16* | (2006.01) | |
| *A61B 17/17* | (2006.01) | |
| *A61B 17/88* | (2006.01) | |

(52) U.S. Cl.
CPC ......... *A61B 17/7208* (2013.01); *A61B 17/1697* (2013.01); *A61B 17/1717* (2013.01); *A61B 17/7266* (2013.01); *A61B 17/8861* (2013.01)
USPC ........................................................ 606/64

(58) Field of Classification Search
CPC ...... A61B 17/72–17/8066; A61B 17/84–17/86
USPC ............ 606/62–68, 70–71, 280, 282, 53, 60, 606/74, 263, 278
See application file for complete search history.

(56) References Cited

U.S. PATENT DOCUMENTS

| | | | | | |
|---|---|---|---|---|---|
| 565,255 | A | * | 8/1896 | Belden | 132/281 |
| 2,489,870 | A | * | 11/1949 | Dzus | 606/310 |
| 4,011,863 | A | * | 3/1977 | Zickel | 606/299 |
| 4,055,172 | A | * | 10/1977 | Ender et al. | 606/62 |
| 4,135,507 | A | * | 1/1979 | Harris | 606/62 |
| 4,169,470 | A | * | 10/1979 | Ender et al. | 606/62 |
| 4,467,793 | A | * | 8/1984 | Ender | 606/62 |
| 4,473,069 | A | * | 9/1984 | Kolmert | 606/64 |
| 4,483,335 | A | * | 11/1984 | Tornier | 606/64 |
| 4,503,847 | A | * | 3/1985 | Mouradian | 606/64 |
| 4,506,662 | A | * | 3/1985 | Anapliotis | 606/62 |
| 4,630,601 | A | * | 12/1986 | Harder et al. | 606/62 |
| 4,838,254 | A | * | 6/1989 | Gauthier | 606/75 |
| 4,915,092 | A | * | 4/1990 | Firica et al. | 606/67 |

(Continued)

OTHER PUBLICATIONS

KIPO/ISA, International Search Report in corresponding international application PCT/US12/42485, completed Dec. 26, 2012.

*Primary Examiner* — Eduardo C Robert
*Assistant Examiner* — Michelle C Eckman
(74) *Attorney, Agent, or Firm* — Stites & Harbison, PLLC; David W. Nagle, Jr.

(57) ABSTRACT

An intramedullary system for managing a fracture of a bone comprises a first rod for insertion into a medullary canal of the bone; and a second rod for insertion into the medullary canal of the bone. The intramedullary system may further include: a first hollow rod segment for receiving an end of the first rod near the first entry point; and a second hollow rod segment for receiving an end of the second rod near the second entry point, wherein the first hollow rod segment and the second hollow rod segment are tamped to force the first curved portion and the second curved portion of the first and second hollow rod segments inside of the bone, along with the first and second rods.

14 Claims, 7 Drawing Sheets

(56) References Cited

U.S. PATENT DOCUMENTS

| | | | |
|---|---|---|---|
| 5,013,314 A * | 5/1991 | Firica et al. | 606/64 |
| 5,116,335 A * | 5/1992 | Hannon et al. | 606/62 |
| 5,135,527 A * | 8/1992 | Ender | 606/62 |
| 5,192,281 A * | 3/1993 | de la Caffiniere | 606/59 |
| 5,281,225 A * | 1/1994 | Vicenzi | 606/62 |
| 5,374,268 A * | 12/1994 | Sander | 606/148 |
| 5,571,103 A * | 11/1996 | Bailey | 606/62 |
| 5,658,283 A * | 8/1997 | Huebner | 606/57 |
| 5,697,934 A * | 12/1997 | Huebner | 606/103 |
| 5,709,682 A * | 1/1998 | Medoff | 606/60 |
| 5,976,134 A * | 11/1999 | Huebner | 606/59 |
| 6,248,109 B1 * | 6/2001 | Stoffella | 606/75 |
| 6,283,964 B1 * | 9/2001 | Weiner | 606/55 |
| 6,302,887 B1 * | 10/2001 | Spranza et al. | 606/916 |
| 6,379,359 B1 * | 4/2002 | Dahners | 606/62 |
| 6,527,775 B1 | 3/2003 | Warburton | |
| 6,660,009 B1 * | 12/2003 | Azar | 606/326 |
| 6,793,659 B2 | 9/2004 | Putnam | |
| 7,037,308 B2 * | 5/2006 | Medoff | 606/319 |
| 7,588,577 B2 | 9/2009 | Fencl et al. | |
| 7,731,718 B2 * | 6/2010 | Schwammberger et al. | 606/71 |
| 7,785,326 B2 * | 8/2010 | Green et al. | 606/64 |
| 7,811,286 B2 * | 10/2010 | Medoff | 606/75 |
| 7,942,877 B2 * | 5/2011 | Medoff | 606/64 |
| 8,083,783 B2 * | 12/2011 | Ullman et al. | 606/329 |
| 8,262,706 B2 * | 9/2012 | Olms et al. | 606/280 |
| 8,328,806 B2 * | 12/2012 | Tyber et al. | 606/62 |
| 8,343,152 B2 * | 1/2013 | Gonzalez-Hernandez | 606/62 |
| 8,398,637 B2 * | 3/2013 | Parsell et al. | 606/71 |
| 8,460,343 B2 * | 6/2013 | Graham | 606/280 |
| 8,475,504 B2 * | 7/2013 | Gillard et al. | 606/281 |
| 8,597,300 B2 * | 12/2013 | Deffenbaugh et al. | 606/86 R |
| 2004/0122428 A1 | 6/2004 | Johnstone | |
| 2004/0225291 A1 * | 11/2004 | Schwammberger et al. | 606/71 |
| 2006/0122613 A1 * | 6/2006 | Kirsch | 606/74 |
| 2006/0200143 A1 | 9/2006 | Warburton | |
| 2007/0173834 A1 * | 7/2007 | Thakkar | 606/62 |
| 2007/0173835 A1 | 7/2007 | Medoff | |
| 2007/0250062 A1 * | 10/2007 | Ara Pinilla et al. | 606/62 |
| 2008/0108989 A1 * | 5/2008 | Parsell et al. | 606/60 |
| 2008/0234679 A1 * | 9/2008 | Sarin et al. | 606/70 |
| 2009/0131937 A1 * | 5/2009 | Medoff | 606/64 |
| 2009/0228049 A1 * | 9/2009 | Park | 606/301 |
| 2009/0312802 A1 * | 12/2009 | DaSilva | 606/304 |
| 2010/0063549 A1 * | 3/2010 | Orbay et al. | 606/281 |
| 2010/0094291 A1 * | 4/2010 | DelBello | 606/62 |
| 2010/0211075 A1 * | 8/2010 | Stone | 606/70 |
| 2010/0318086 A1 * | 12/2010 | Winemaker | 606/70 |
| 2011/0009912 A1 * | 1/2011 | Gonzalez-Hernandez et al. | 606/328 |
| 2013/0096559 A1 * | 4/2013 | Katrana et al. | 606/71 |
| 2013/0237987 A1 * | 9/2013 | Graham | 606/64 |

\* cited by examiner

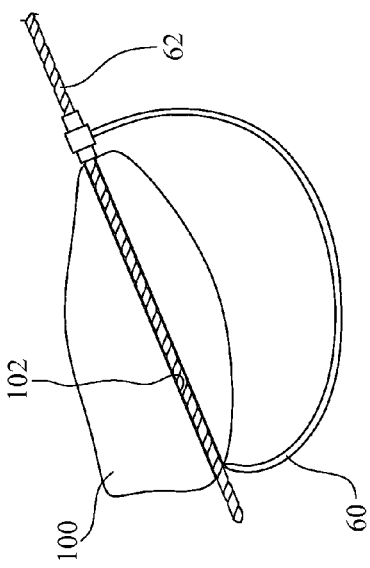
FIG. 1
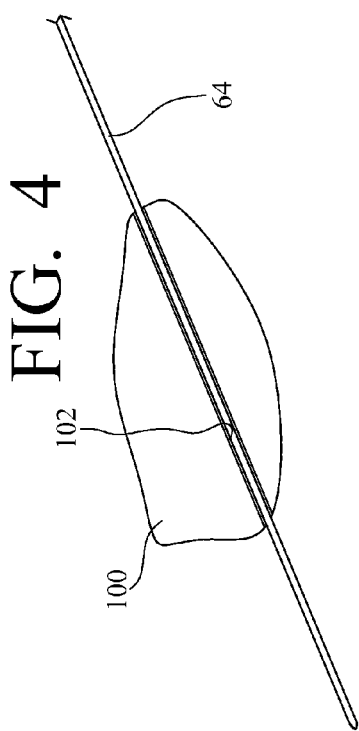
FIG. 2
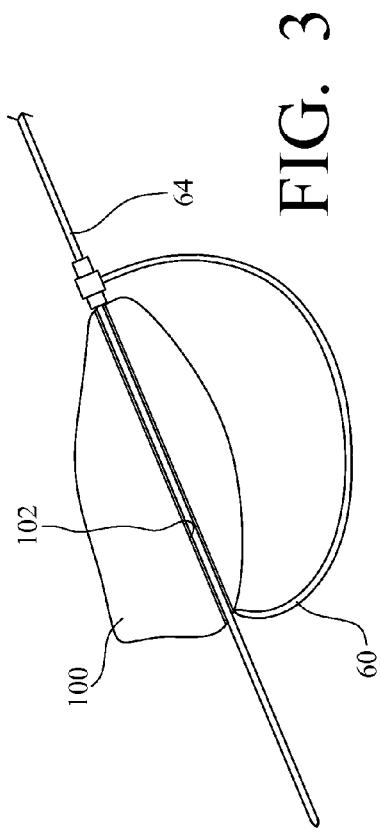
FIG. 3
FIG. 4

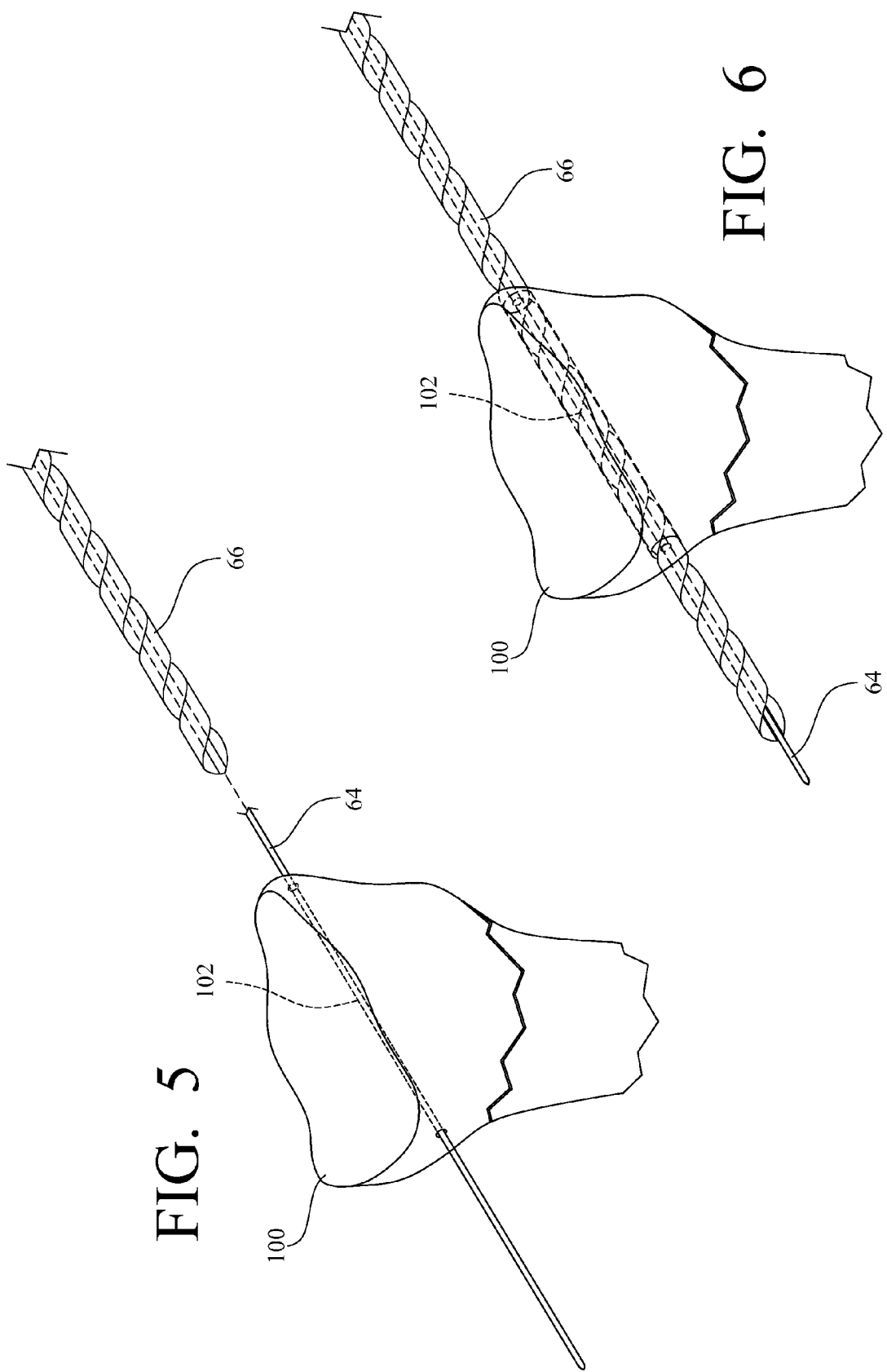

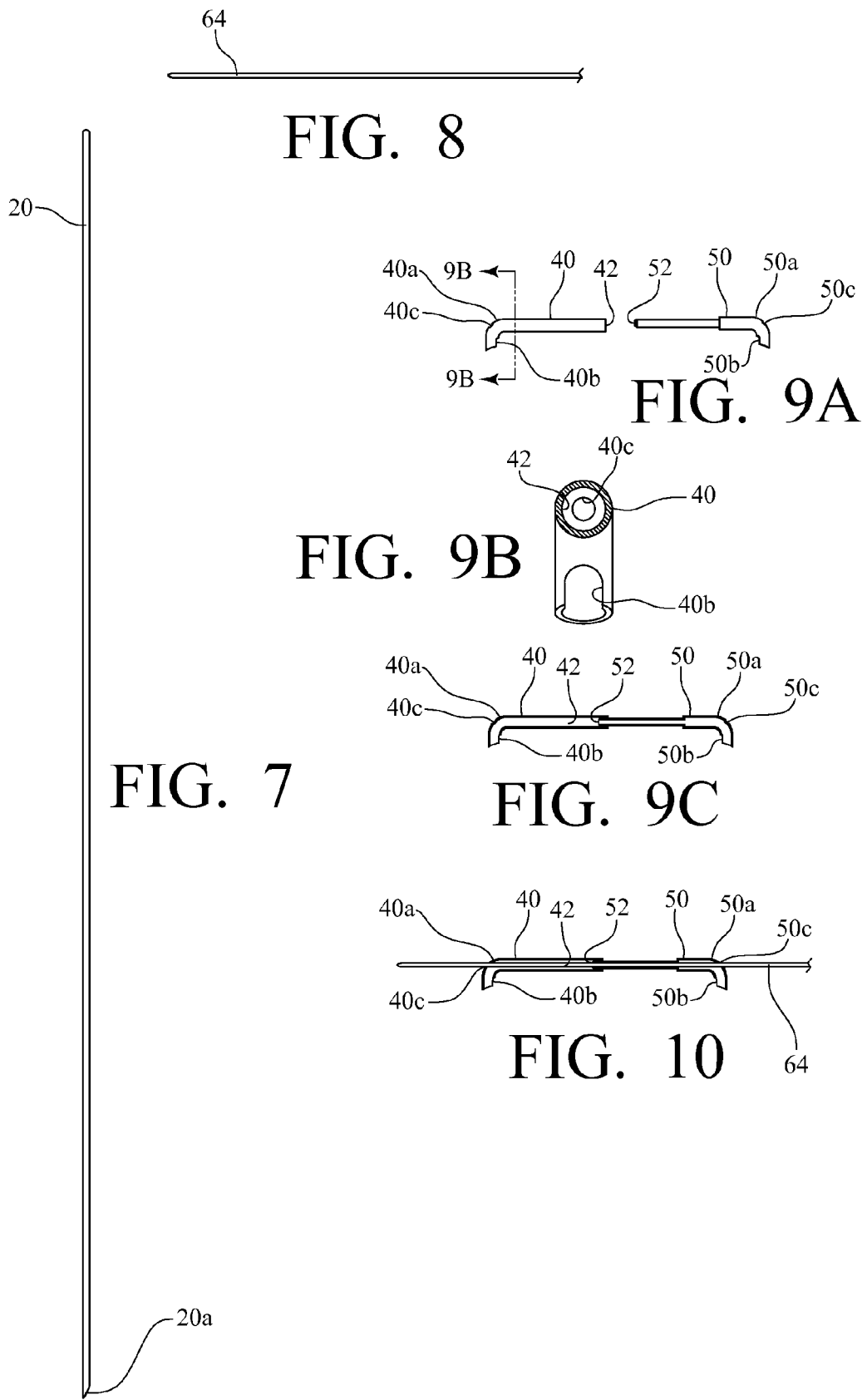

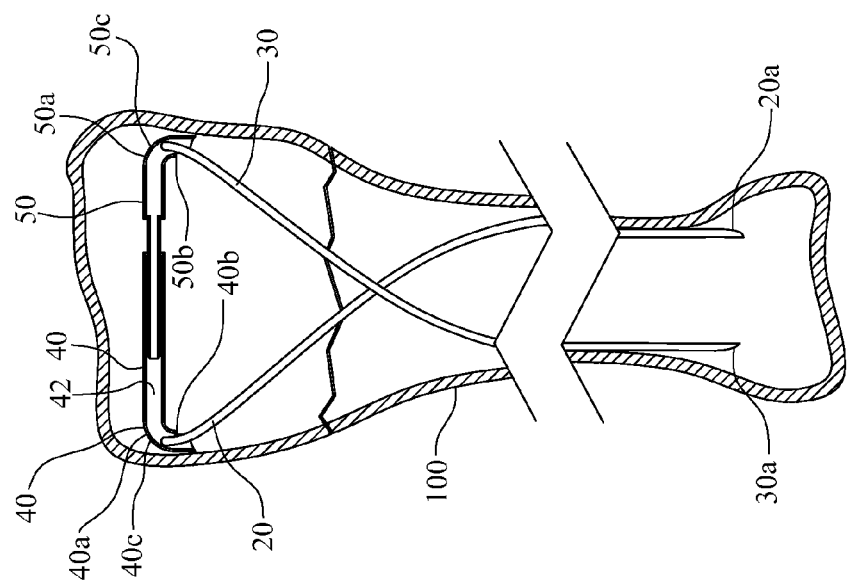
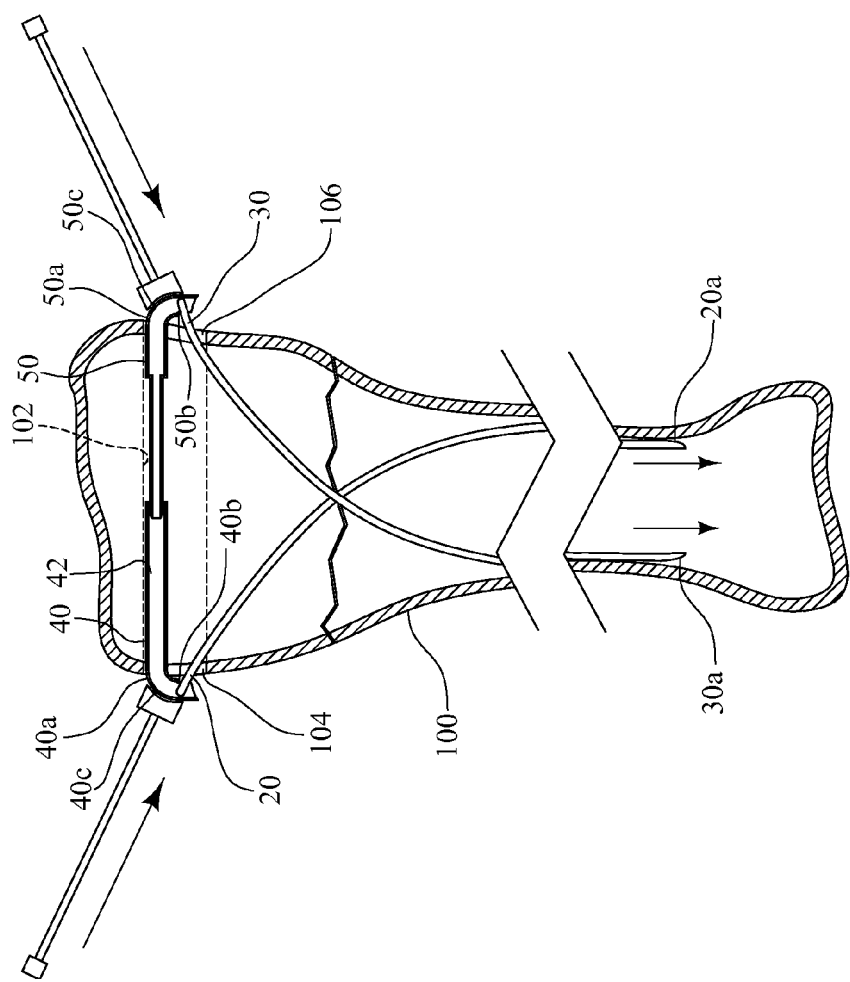
FIG. 14
FIG. 15

INTRAMEDULLARY SYSTEM FOR MANAGING A BONE FRACTURE

CROSS-REFERENCE TO RELATED APPLICATIONS

The present application claims priority to U.S. Provisional Patent Application Ser. No. 61/496,658 filed on Jun. 14, 2011, the entire disclosure of which is incorporated herein by reference.

BACKGROUND OF THE INVENTION

The present invention pertains to the management of a bone fracture, and, more particularly, the use of an intramedullary system for managing a distal radius or similar bone fracture.

A distal radius fracture is a bone fracture of the radius in the forearm, and indeed, it is one of the most common bone fractures. Because of its proximity to the wrist joint, such a fracture is often referred to as a wrist fracture.

The management of distal radius fractures has evolved through many phases. In the 1950's and 1960's, closed reduction and immobilization (i.e., casting) were preferred forms of treatment. Unfortunately, in a large proportion of displaced distal radius fractures, casting was unable to maintain the alignment of the fragments and the reduction. Therefore, percutaneous pinning was added as an adjunct, and many variations of percutaneous pinning techniques were used.

In the 1980's, the management of distal radius fractures was mostly through external fixation. Many types of external fixation techniques were developed and used, including mobile external fixation systems. In addition to the external fixation, percutaneous fixation was also used in some circumstances.

In the 1990's, the trend shifted toward internal fixation, where a plate was applied to the dorsal surface of the radius. Although this form of internal fixation was generally successful, there were many problems with placement of thick metal plates on the dorsal surface of the radius where there was very little space for a plate. There were many reports of tendonitis and tendon rupture due to such plates rubbing against the tendons.

In the 2000's, the trend shifted toward putting the plate on the palmar surface of the radius—volar (palmar) radial plating. Volar locked plate systems are now a very common method of management of distal radius fractures around the world.

Although volar locked plate systems have improved the outcome of distal radius fractures in the short term, there is currently no firm evidence that this method of management of a distal radius fracture is any better than prior methods, such as external fixation, in the long run. There are also certain disadvantages in using volar locked plate systems, including increased possibility of tendon ruptures and the expense of management. Furthermore, as most distal radius fractures are extraarticular, some have opined that fixing all fractures with a strong, locked volar plate is "overkill" with respect to many distal radius fractures.

SUMMARY OF THE INVENTION

The present invention is an intramedullary system for managing a distal radius or similar bone fracture. In such an intramedullary system, the metal components are not exposed, but rather are hidden inside the medullary canal of the bone. The intramedullary system thus attempts to address some of the disadvantages of volar locked plate systems, while ensuring that the fracture is properly held in position until it heals.

An exemplary intramedullary system made in accordance with the present invention includes a first rod and a second rod that are inserted into the radius from the distal end of the radius. In practice, a small-bore drill is used to create a channel through the radius in a direction generally perpendicular to a longitudinal axis of the bone. A guide wire is then inserted through the channel from the radial styloid to the ulnar side of the radius. A larger-bore, cannulated drill is then driven through the bone from the radial to the ulnar side of the radius on the guide wire to increase the size of the channel.

The first rod is then introduced through a first entry point at one end of the channel and into the medullary canal of the radius. A beveled end of the first rod helps it slide down the radial cortex as it is advanced into the medullary canal. Specifically, as it enters the medullary canal, the beveled end of the first rod strikes the inside of the opposite cortex of the radius and then slides down the radius toward the proximal end of the radius. Similarly, the second rod is introduced through an entry point at the other end of the channel and into the medullary canal of the radius. Like the first rod, a beveled end of the second rod strikes the inside of the opposite cortex of the radius and then slides down the radius toward the proximal end of the radius. The first and second rods preferably cross one another just proximal to the fracture.

An exemplary intramedullary system made in accordance with the present invention may further include first and second hollow rod segments. Each of the first and second hollow rod segments is mounted and advanced over the guide wire. The first hollow rod segment defines an internal cavity that is configured and sized to receive an end of the second hollow rod segment, thus allowing the first hollow rod segment and the second hollow rod segment to be mated with one another. Furthermore, the first hollow rod segment terminates in a curved portion at its opposite end with a slot defined along the internal surface of this curved portion. The second hollow rod segment similarly terminates in a curved portion at its opposite end with a slot defined along the internal surface of this curved portion. Finally, there is a central passageway through the entire length of the first hollow rod segment, and there is a corresponding central passageway through the entire length of the second hollow rod segment.

In practice, once the first and second rods have been introduced into the medullary canal of the radius, each of the first and second hollow rod segments is advanced over the guide wire. The end of the first rod extending from the entry point is engaged by the slot defined along the internal surface of the curved portion of the first hollow rod segment. Similarly, the end of the second rod extending from the entry point is engaged by the slot defined along the internal surface of the curved portion of the second hollow rod segment. Each of the first and second hollow rod segments is tamped to force the curved portions inside of the radius, which also forces the first and second rods inside of the radius. Once so positioned inside of the radius, the intramedullary system effectively provides a three-point fixation system that stabilizes the fracture and holds the fracture in a reduced position. At the same time, the intramedullary system does not allow the fracture to collapse by maintaining the height and the alignment of the fracture until it completely heals.

DESCRIPTION OF THE DRAWINGS

FIG. 1 is a perspective view of the distal end of a radius, illustrating a distal radius fracture;

FIG. 2 is a top view of the radius of FIG. 1, illustrating the use of an alignment guide and small-bore drill to create a channel through the radius;

FIG. 3 is a top view similar to FIG. 2, illustrating the insertion of a guide wire through the alignment guide and through the radius from the radial styloid to the ulnar side;

FIG. 4 is a top view similar to FIG. 2, but with the alignment guide removed;

FIGS. 5 and 6 are perspective views similar to FIG. 1, illustrating the use of a larger-bore, cannulated drill to increase the size of the channel through the radius from the radial styloid to the ulnar side;

FIG. 7 is a view of one of the rods of an exemplary intramedullary system made in accordance with the present invention;

FIG. 8 is a view of a guide wire for use with an exemplary intramedullary system;

FIG. 9A is a side view of the hollow rod segments of an exemplary intramedullary system;

FIG. 9B is a sectional view of one of the hollow rod segments taken along line 9B-9B of FIG. 9A;

FIG. 9C is another side view of the hollow rod segments shown in FIG. 9A, but further illustrating the hollow rod segments being mated to one another;

FIG. 10 is a side view of the hollow rod segments of FIG. 9A as placed over the guide wire of FIG. 8 and mated to one another; and FIGS. 11-16 are side sectional views of the radius of FIG. 1, illustrating the use of an exemplary intramedullary system.

DETAILED DESCRIPTION OF THE INVENTION

The present invention is an intramedullary system for managing a distal radius or similar bone fracture. In such an intramedullary system, the metal components are not exposed, but rather are hidden inside the medullary canal of the bone. The intramedullary system thus attempts to address some of the disadvantages of volar locked plate systems, while ensuring that the fracture is properly held in position until it heals.

Figure 11:
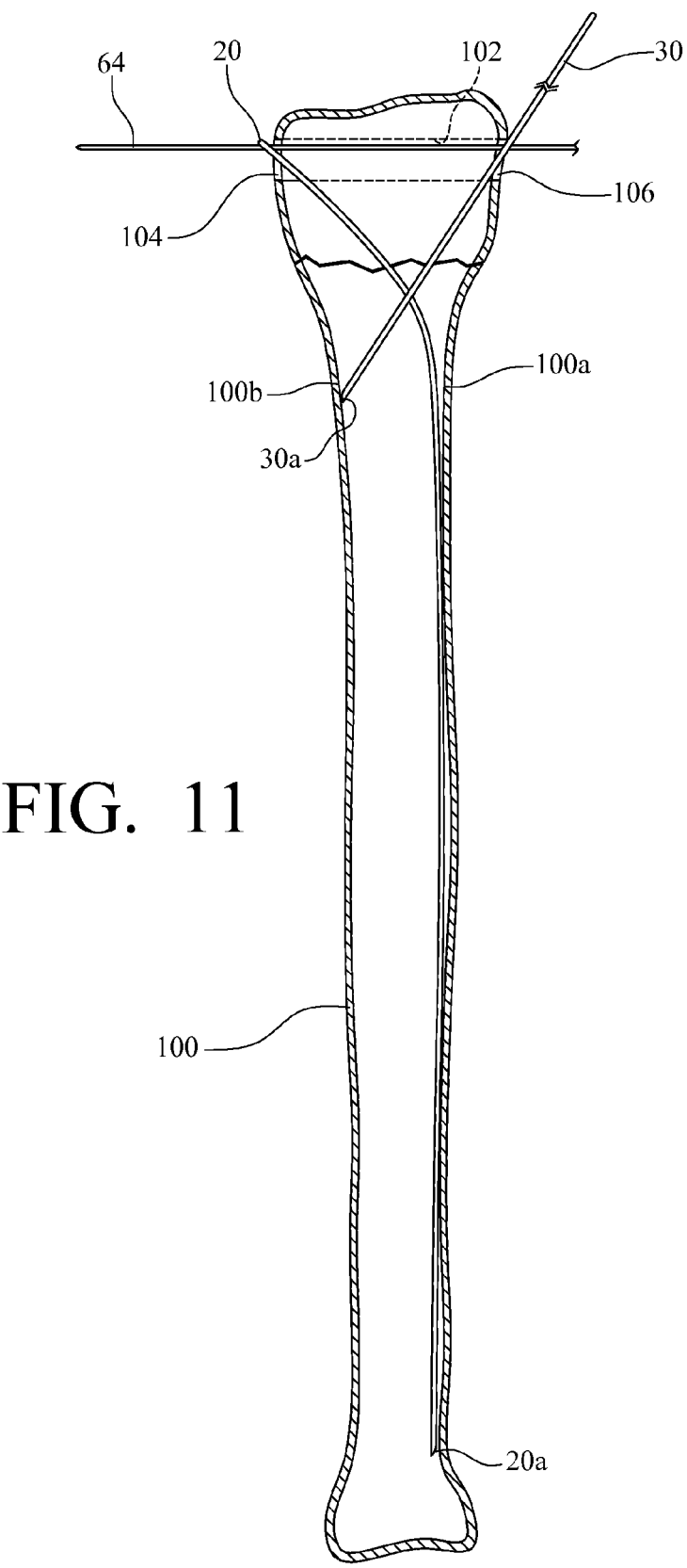

Referring first to FIG. 11, an exemplary intramedullary system 10 made in accordance with the present invention includes a first rod 20 and a second rod 30 that are inserted into the radius 100 from the distal end of the radius 100.

Referring now to FIGS. 1-6, it is preferred that a small incision is made to access the radial styloid, and after moving the tendons aside, an alignment guide 60 is applied from the radial styloid to the ulnar side just dorsal to the sigmoid notch of the radius 100, adjacent to which another small incision is made and the bone is exposed. Once the alignment guide 60 is applied to these points, a small-bore drill 62 is used to create a channel 102 through the radius 100 in a direction generally perpendicular to a longitudinal axis of the bone, as shown in FIG. 2. A guide wire 64 is then inserted through the alignment guide 60 and through the channel 102, from the radial styloid to the ulnar side of the radius 100, as shown in FIG. 3. The alignment guide 60 is then removed, as shown in FIG. 4. A larger-bore, cannulated drill 66 is then driven through the bone from the radial to the ulnar side of the radius 100 on the guide wire 64, as shown in FIGS. 5 and 6 to increase the size of the channel 102.

FIG. 7 is a view of the first rod 20 (which is substantially identical to the second rod 30) of the exemplary intramedullary system 10. As shown, in the exemplary embodiment, the first rod 20 has a beveled end 20a.

Referring now to FIG. 11, in use, the first rod 20 is introduced through a first entry point 104 at one end of the channel 102 defined through the radius 100 and into the medullary canal of the radius 100. The beveled end 20a of the first rod 20 helps it slide down the radial cortex as it is advanced into the medullary canal. Specifically, as it enters the medullary canal, the beveled end 20a of the first rod 20 strikes the inside of the opposite cortex of the radius 100 (i.e., a first portion 100a of the cortex of the bone) and then slides down the radius 100 toward the proximal end of the radius 100. Similarly, the second rod 30 is introduced through an entry point 106 at the other end of the channel 102 defined through the radius 100 and into the medullary canal of the radius 100. Like the first rod 20, the beveled end 30a of the second rod 30 strikes the inside of the opposite cortex of the radius 100 (i.e., a second portion 100b of the cortex of the bone) and then slides down the radius 100 toward the proximal end of the radius 100. Thus, and as shown in FIGS. 12-16, the first and second rods 20, 30 cross one another just proximal to the fracture.

Referring now to FIGS. 9A-9C and 10, the exemplary intramedullary system further includes first and second hollow rod segments 40, 50. Each of the first and second hollow rod segments 40, 50 is mounted and advanced over the guide wire 64. As perhaps best shown in FIGS. 9A-9C, the first hollow rod segment 40 defines an internal cavity 42 that is configured and sized to receive an end 52 of the second hollow rod segment 50, thus allowing the first hollow rod segment 40 and the second hollow rod segment 50 to be mated with one another. Furthermore, the first hollow rod segment 40 terminates in a curved portion 40a at its opposite end with a slot 40b defined along the internal surface of this curved portion 40a. The second hollow rod segment 50 similarly terminates in a curved portion 50a at its opposite end with a slot 50b defined along the internal surface of this curved portion 50a. Finally, and as best shown in FIGS. 9C and 10, there is a central passageway 40c through the entire length of the first hollow rod segment 40, and there is a corresponding central passageway 50c through the entire length of the second hollow rod segment 50. Thus, when the first hollow rod segment 40 and the second hollow rod segment 50 are mated, they both may be advanced over a guide wire 64, as further described below.

Figure 13:
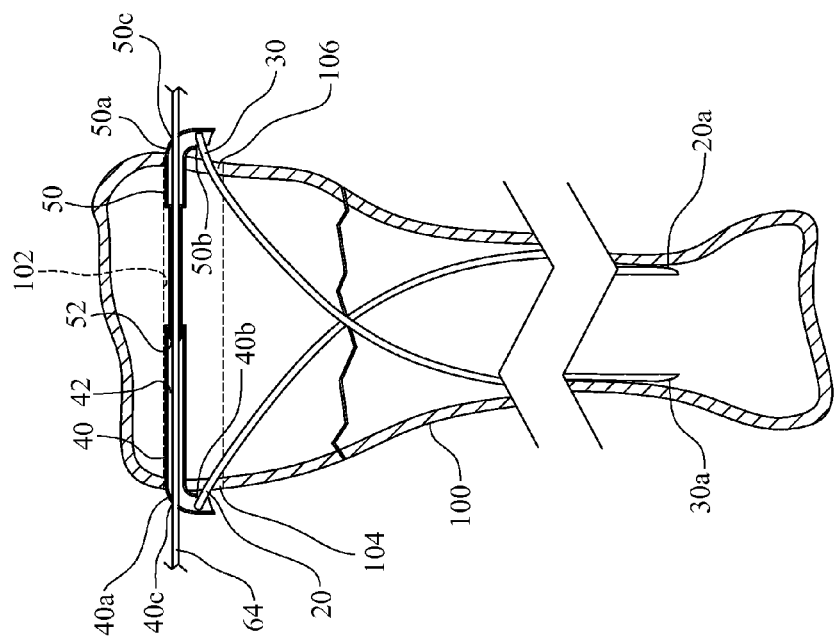
Figure 12:
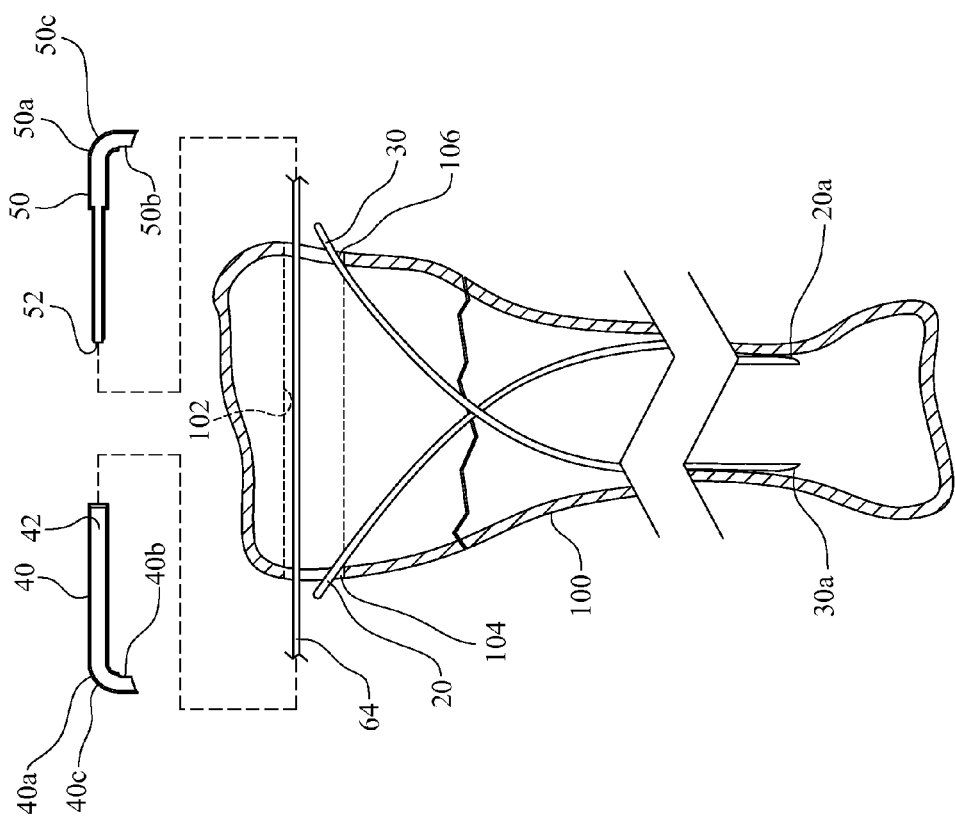
Figure 16:
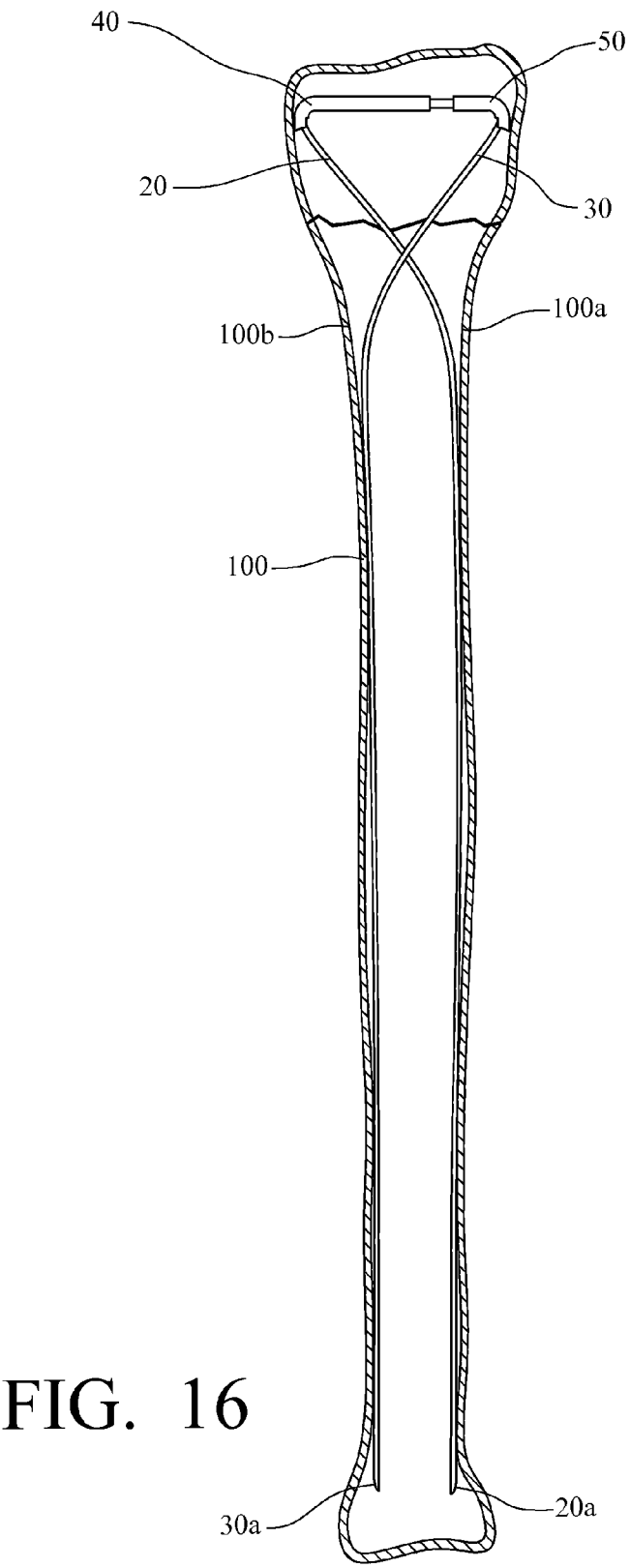

Referring now to FIGS. 12-16, once the first and second rods 20, 30 have been introduced into the medullary canal of the radius 100, each of the first and second hollow rod segments 40, 50 is advanced over the guide wire 64. The end of the first rod 20 extending from the entry point 104 is engaged by the slot 40b defined along the internal surface of the curved portion 40a of the first hollow rod segment 40, as shown in FIG. 13. Similarly, the end of the second rod 30 extending from the entry point 106 is engaged by the slot 50b defined along the internal surface of the curved portion 50a of the second hollow rod segment 50, as also shown in FIG. 13. Each of the first and second hollow rod segments 40, 50 is tamped to force the curved portions 40a, 50a inside of the radius 100, which also forces the first and second rods 20, 30 inside of the radius 100, as shown in FIGS. 14 and 15. Once so positioned inside of the radius 100, the intramedullary system 10 effectively provides a three-point fixation system that stabilizes the fracture and holds the fracture in a reduced position, as shown in FIG. 16. At the same time, the intramedullary system 10 does not allow the fracture to collapse by maintaining the height and the alignment of the fracture until it completely heals.

As a further refinement, it is also contemplated that the intramedullary system 10 of the present invention could be used in combination with extramedullary fixation systems and techniques to treat more complex fractures.

One of ordinary skill in the art will recognize that additional embodiments are also possible without departing from the teachings of the present invention. This detailed description, and particularly the specific details of the exemplary embodiment disclosed therein, is given primarily for clarity of understanding, and no unnecessary limitations are to be understood therefrom, for modifications will become obvious to those skilled in the art upon reading this disclosure and may be made without departing from the spirit or scope of the invention.

What is claimed is:

1. An intramedullary system for managing a fracture of a bone, comprising:
 a first rod for insertion into a medullary canal of the bone, the first rod being configured such that, upon entering the medullary canal from a first entry point, the first rod contacts a first portion of a cortex of the bone opposite the first entry point and slides downwardly along the first portion of the cortex of the bone;
 a second rod for insertion into the medullary canal of the bone, the second rod being configured such that, upon entering the medullary canal from a second entry point, the second rod contacts a second portion of the cortex of the bone opposite the second entry point and slides downwardly along the second portion of the cortex of the bone; and
 a connector for insertion into the medullary canal and configured to connect the first rod to the second rod inside the medullary canal of the bone, wherein the connector comprises:
 a first hollow rod segment for receiving an end of the first rod near the first entry point; and
 a second hollow rod segment for receiving an end of the second rod near the second entry point;
 wherein the first hollow rod segment and the second hollow rod segment are configured to mate with each other upon positioning of the first hollow rod segment and the second hollow rod segment inside the medullary canal of the bone.

2. The intramedullary system as recited in claim 1, wherein the first hollow rod segment defines an internal cavity for receiving an end of the second hollow rod segment.

3. The intramedullary system as recited in claim 1, wherein the first hollow rod segment terminates in a first curved portion having a slot defined along an internal surface of the first curved portion for receiving the end of the first rod near the first entry point; and wherein the second hollow rod segment terminates in a second curved portion having a slot defined along an internal surface of the second curved portion for receiving the end of the second rod near the second entry point.

4. The intramedullary system as recited in claim 1, wherein a central passageway is defined through the first hollow rod segment and a corresponding central passageway is defined through the second hollow rod segment, such that, the first hollow rod segment and the second hollow rod segment are configured to be advanced over a guide wire.

5. An intramedullary system for managing a fracture of a bone, comprising:
 a first rod for insertion into a medullary canal of the bone, the first rod being configured such that, upon entering the medullary canal from a first entry point, the first rod contacts a first portion of a cortex of the bone opposite the first entry point and slides downwardly along the first portion of the cortex of the bone;
 a second rod for insertion into the medullary canal of the bone, the second rod being configured such that, upon entering the medullary canal from a second entry point, the second rod contacts a second portion of the cortex of the bone opposite the second entry point and slides downwardly along the second portion of the cortex of the bone;
 a first hollow rod segment for receiving an end of the first rod near the first entry point; and
 a second hollow rod segment for receiving an end of the second rod near the second entry point;
 wherein the first hollow rod segment and the second hollow rod segment are configured to slidably mate with each other upon positioning of the first hollow rod segment and the second hollow rod segment inside the medullary canal of the bone.

6. The intramedullary system as recited in claim 5, wherein the first rod and the second rod are further configured to cross one another within the medullary canal proximal to the fracture.

7. The intramedullary system as recited in claim 5, wherein the first rod and the second rod each have a beveled end.

8. The intramedullary system as recited in claim 5, wherein the first hollow rod segment defines an internal cavity for receiving an end of the second hollow rod segment to mate the first hollow rod segment and the second hollow rod segment.

9. The intramedullary system as recited in claim 5, wherein the first hollow rod segment terminates in a first curved portion having a slot defined along an internal surface of the first curved portion for receiving the end of the first rod near the first entry point; and wherein the second hollow rod segment terminates in a second curved portion having a slot defined along an internal surface of the second curved portion for receiving the end of the second rod near the second entry point.

10. The intramedullary system as recited in claim 5, wherein a central passageway is defined through the first hollow rod segment and a corresponding central passageway is defined through the second hollow rod segment, such that, the first hollow rod segment and the second hollow rod segment are configured to be advanced over a guide wire.

11. A method for managing a fracture of a bone, comprising the steps of:
 providing an intramedullary system, including a first rod for insertion into a medullary canal of the bone, a second rod for insertion into the medullary canal of the bone, a first hollow rod segment for insertion into the medullary canal of the bone, and a second hollow rod segment for insertion into the medullary canal of the bone;
 creating a channel in the bone extending from a first entry point to a second entry point, and in a direction generally perpendicular to a longitudinal axis of the bone;
 inserting a guide wire through the channel;
 inserting the first rod into the medullary canal of the bone through the first entry point and advancing the first rod into the medullary canal of the bone such that it contacts a first portion of a cortex of the bone opposite the first entry point and slides downwardly along the first portion of the cortex of the bone;
 inserting the second rod into the medullary canal of the bone through the second entry point and advancing the second rod into the medullary canal of the bone such that it contacts a second portion of the cortex of the bone opposite the second entry point and slides downwardly along the second portion of the cortex of the bone;
 inserting a first hollow rod segment into the channel over the guide wire, said first hollow rod segment receiving an end of the first rod near the first entry point; and inserting a second hollow rod segment into the channel over the guide wire, said second hollow rod segment receiving an end of the second rod near the second entry point;

wherein the first hollow rod segment terminates in a first curved portion having a slot defined along an internal surface of the first curved portion for receiving the end of the first rod, and wherein the second hollow rod segment terminates in a second curved portion having a slot defined along an internal surface of the second curved portion for receiving the end of the second rod.

12. The method as recited in claim 11, wherein the first rod and the second rod are inserted and advanced into the medullary canal of the bone such that the first rod and the second rod cross one another within the medullary canal proximal to the fracture.

13. The method as recited in claim 11, and further comprising the step of tamping the first hollow rod segment and the second hollow rod segment to thereby force the first curved portion and the second curved portion of the first and second hollow rod segments inside of the bone, along with the first and second rods.

14. The method as recited in claim 11, wherein the first rod and the second rod each have a beveled end.

\* \* \* \* \*